US005591836A

United States Patent [19]

Mazur et al.

[11] Patent Number: 5,591,836

[45] Date of Patent: Jan. 7, 1997

[54] CHOLESTEROL LOWERING COMPOUNDS

[75] Inventors: Adam W. Mazur; Stanislaw Pikul; Bruce P. Daggy, all of Cincinnati, Ohio

[73] Assignee: The Procter & Gamble Company, Cincinnati, Ohio

[21] Appl. No.: 133,822

[22] Filed: Oct. 7, 1993

Related U.S. Application Data

[63] Continuation of Ser. No. 771,668, Oct. 4, 1991, abandoned.

[51] Int. Cl.$^6$ .................. C07J 17/00; A61K 31/705; C07H 15/24
[52] U.S. Cl. .................. 536/6.1; 536/5; 514/26; 514/54; 514/61; 514/824
[58] Field of Search .................. 536/5, 6.1; 514/26, 514/54, 61

[56] References Cited

U.S. PATENT DOCUMENTS

| | | | |
|---|---|---|---|
| 3,865,939 | 2/1975 | Jandacek | 424/238 |
| 4,242,502 | 12/1980 | Malinow et al. | 536/5 |
| 4,461,762 | 7/1984 | Malinow | 424/182 |
| 4,524,067 | 6/1985 | Arichi et al. | 514/33 |
| 4,602,003 | 7/1986 | Malinow | 514/26 |
| 4,602,005 | 7/1986 | Malinow | 514/26 |
| 5,041,541 | 8/1991 | Mazur | 536/1.1 |

FOREIGN PATENT DOCUMENTS 61-249364 of 1985 Japan.

OTHER PUBLICATIONS

Ohominami, et al. CA 96:210724X (1981).
Moon et al. CA 101; 204131G (1984).
Stone CA 102; 165757Q (1985).
Sid hu et al., Brit. J. Nutri. 55, 643–649 (1986).
Ulloa, et al. Index Medicus, 86026393 (1985).
Malinow, Annal. N.Y. Academy of Sciences, 454, 23–27 (1985).
Malinow, Amer. J. Nutri., 30, 2061–2067 (1977).
Malinow, Amer. J. Nutri 32 (9), 1810–2 (1979).
Story, Amer. J. Nutri. 39 (6) 917–29 (1984).

*Primary Examiner*—John Kight, III
*Assistant Examiner*—Howard C. Lee
*Attorney, Agent, or Firm*—Rose Ann Dabek; Richard A. Hake; Milton B. Graff, IV

[57] ABSTRACT

Disclosed are novel saponins containing 5-C-hydroxymethylhexose and a sterol or triterpene. These materials, when consumed by humans and animals, lower the cholesterol level in the blood. These compounds can be administered as pharmaceutical preparation to the diet, or incorporated into food compositions.

17 Claims, No Drawings

CHOLESTEROL LOWERING COMPOUNDS

This is a continuation of application Ser. No. 07/771,668, filed on Oct. 4, 1991, now abandoned.

TECHNICAL FIELD

This invention relates to novel 5-C-hydroxymethyl hexose-derivatives of sterols and their use to lower both serum cholesterol and serum triglyceride levels. These novel saponins are resistant to absorption and metabolism.

BACKGROUND OF THE INVENTION

Saponins are a type of glycoside found in nature. A saponin is composed of a sapogenin and a sugar. The sugar can be a monosaccharide or an oligosaccharide. The sapogenin is a steroid or a triterpene.

The saponins found in soybeans, alfalfa, and ginseng have been studied extensively for their effect of lowering cholesterol. Both the animal's ability to absorb cholesterol as well as its level of serum cholesterol are reduced. The work on soybean saponins and lipid metabolism was performed by Ohominami, et al at the School of Medicine, Ehime University of Japan in 1981. This work is abstracted in CA96; 210724X. The work on ginseng is disclosed in CA101; 204131G. This work was done by Moon et al, University of Seoul, Korea. The effect of dietary alfalfa sprouts and alfalfa saponins is the subject of a dissertation by David L. Stone, University of California, Berkeley (CA 102; 165757Q). A mechanism for hypocholesterolemic activity of saponins was published by Sidhu et al in the *British Journal of Nutrition* in 1986.

Japanese Patent 86/249,364 assigned Osaka Yakuhin Kenky describes the use of a soyasaponin for preventing thrombosis. U.S. Pat. No. 4,242,502 issued to Malinow et al (assigned United States, 1980) relates to the use of saponins to inhibit cholesterol absorption. According to this reference, modification of the oligosaccharide portion of the saponin by hydrolysis under mild acid conditions affects the saponins' ability to affect cholesterol absorption.

U.S. Pat. No. 4,524,067 issued to Arichi et al (Osaka Chemical Laboratory, 1985) discloses the use of bean saponins for lowering cholesterol.

Ulloa et al, *Biochim Biophys Acta*, (1985), 837 (2) pp. 181–9 as abstracted in *Index Medicus* describes experiments in which different plant steroids, including saponins, increase biliary cholesterol secretion.

U.S. Pat. No. 4,602,003 issued to Malinow (1986) describes synthetic sapogenin and sterol compounds which inhibit the absorption of cholesterol and are used to treat hypercholesterolemia. These compounds are synthetic glycosides of tigogenin, diosgenin, smilagenin, and the like. Cellobiose-tigogenin and cellobiose-diosgenin were also made as were the ester derivatives.

U.S. Pat. No. 4,602,005 issued to Malinow (1986) is related to the 4,602,003 patent. Tigogenin cellobioside is described as being particularly effective for treating hypercholesterolemia and atherosclerosis.

The liver plays a central role in the regulation of blood cholesterol concentration and flux. It has long been recognized that manipulation of the enterohepatic circulation of cholesterol and/or bile acids is a means to change blood cholesterol levels, particularly low density lipoprotein cholesterol (LDL-C) levels, via influences on hepatic metabolism. Agents which bind or otherwise prevent the absorption of cholesterol and bile acids across the gut wall, if given at a sufficient dose, will cause the liver to up-regulate the LDL receptor. The resultant drop in LDL concentrations is generally believed to provide significant therapeutic benefits.

While it is well known that saponins have a cholesterol lowering benefit, it is also well known that these materials hydrolyze in the digestive system. When the sugar moiety is removed, i.e., the glycosidic linkage is cleaved, the cholesterol is no longer removed. Therefore, a saponin derivative which does not hydrolyze in the stomach or intestine would be highly desirable. Such a compound could even be derived from cholesterol.

Surprisingly it has been found that derivatizing a sterol with a 5-C-hydroxymethyl substituted sugar provides a saponin derivative which is not hydrolyzed in the stomach or intestine, but still functions to lower cholesterol and serum triglycerides. The 5-C-hydroxymethyl sugars are the subject of U.S. Pat. No. 5,041,541 (1991).

It is an object of this invention to provide novel saponins which are poorly hydrolyzed in the digestive tract. It is a further object of this invention to provide novel compounds which lower the cholesterol absorbed by the body and also lower serum cholesterol levels in animal and human subjects. These and other objects will be evident from the discussion herein.

All percentages are by weight unless otherwise indicated.

SUMMARY OF THE INVENTION

The novel saponins of the present invention encompass 5-C-hydroxymethylhexose mono-, di- or trisaccharides which are bonded to sterols through a glycosidic linkage. Derivatives of these 5-C-hydroxymethyl carbohydrates can also be used, including di- and trisaccharides containing at least one simple sugar linkage from the above-mentioned novel carbohydrates bonded by a glycosidic linkage to a sterol. The sterols are selected from the group of spirostanols such as diosgenin and tigogenin, as well as others including, cholesterol, α-sitosterol, β-sitosterol, stigmasterol, sitostanol, ergosterol and campesterol.

These novel saponins when orally ingested by human or animal subjects result in lower serum cholesterol levels. They are also expected to protect against atherosclerosis and its sequelae.

Also included in this invention are pharmaceutically acceptable compositions containing these sterol derivatives in unit dosage form.

DETAILED DESCRIPTION OF THE INVENTION

Definitions

The term "comprising" as used herein encompasses the terms "consisting of" and "consisting essentially of".

The terms "novel saponins" and "hydroxymethyl saponins" as used herein refer to the 5-C-hydroxylmethyl derivatives of the hexoses and their stereoisomers which are bonded to a sterol to provide a saponin. The bond is through a glycosidic linkage. Monosaccharides, di- and trisaccharide derivatives of the hexoses may be used to derivatize the sterol.

The term "sterol" as used herein refers to natural or synthetic plant or animal sterols or triterpenes. This includes the phytosterols and the mycosterols as well as cholesterol. For a more detailed discussion of sterols see for example, Nes, W. D., Parish, E. J. Ed., "Analysis of Sterols and Other Biologically Significant Steroids", Academic Press, Inc.

(1989). Preferred sterols are selected from the group of diosgenin, stigmastanol, tigogenin, cholesterol, α-sitosterol, β-sitosterol, stigmasterol, ergosterol, campesterol, oleanoic acids, soyasapogenols, protoascigenin, togenols, protoparaxadiols, and protopanaxadiols.

The term "galactose oxidase" as used herein refers to D-galactose:oxygen 6-oxidoreductase which is identified as E. C. 1.1.3.9 or as Chemical Abstracts Registry. Number 9028-79-9.

The term "catalase", as used herein, refers to $H_2O_2:H_2O_2$ oxidoreductase which is identified as E. C. 1.11.1.6. Catalase is an enzyme which decomposes hydrogen peroxide. These enzymes occur in both plant and animal cells.

The term "hexose" means a carbohydrate containing six carbons. This term encompasses both aldehyde-containing hexoses (aldohexoses) and ketone-containing hexoses (ketohexoses).

The term "aldohexoses" refers to the group of sugars whose molecule contains six carbon atoms, one aldehyde group and five alcohol groups. The sixteen stereoisomers of the aldohexose series are D-allose, D-altrose, D-glucose, D-mannose, D-gulose, D-idose, D-galactose, D-talose, L-allose, L-altrose, L-glucose, L-mannose, L-gulose, L-idose, L-galactose and L-talose. These sugars exist in solution as an equilibrium mixture of several "tautomeric forms": a pyran-ring form; a furan-ring form; or a straight-chain aldehyde form. Aldohexoses may also occur in an α or β anomeric configuration, depending on the position of the C-1 hydroxyl group.

The term "D-ketohexose" refers to the group of sugars which contain six carbon atoms, one ketone group and five alcohol groups. The eight stereoisomers are D- and L-isomers of psicose, fructose, sorbose and tagatose. Like the aldohexoses, these ketohexoses can exist in solution as an equilibrium mixture of several "tautomeric forms": pyran-ring; a furan ring and a straight chain ketone form.

Specific compounds and compositions to be used in these processes must, accordingly, be pharmaceutically acceptable. As used herein, a "pharmaceutically acceptable" component is one that is suitable for use with humans and/or animals without undue adverse side effects (such as toxicity, irritation, and allergic response) commensurate with a reasonable benefit/risk ratio. Further, as used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will vary with such factors as the particular condition being treated, the physical condition of the patient, the duration of the treatment, the nature of concurrent therapy (if any), and the specific formulations employed.

DESCRIPTION OF THE NOVEL COMPOUNDS

5-C-hydroxymethyl aldohexose mono-, di- or trisaccharides can be used to make the sterols of the present invention. Preferred 5-C-hydroxymethylaldohexose derivatives are those of galactose, glucose, and mannose. Due to the relative ease of synthesizing galactose-based compounds, derivatives of D-galactose are the most preferred compounds. These can be in the form of aldohexopyranoses or aldohexofuranoses.

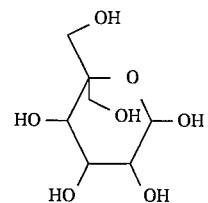

Other monosaccharides based on the ketohexose derivatives are:

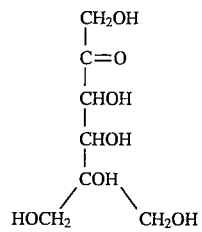 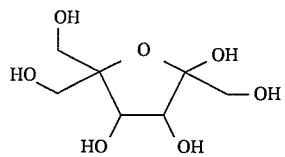

Preferred embodiments are 5-C-hydroxymethyl derivatives of fructose and sorbose, due to the availability of natural sugars. Preferred disaccharides comprise at least one 5-C-hydroxymethylaldohexose or 5-C-hydroxymethylketohexose.

The sterol derivatives of this invention contain at least one 5-C-hydroxymethyl sugar group (i.e., monosaccharides, monosaccharide derivatives) from the monosaccharides discussed above (I or II) covalently bound through glycoside linkages.

The sterols contain an alcohol group which reacts with the sugar to form a glycosidic bond.

The synthesis of the sterol glycosides involves the reaction of an acetylated or other protected 5-C-hydroxymethyl hexose with a sterol in the presence of a catalyst and an inert solvent. The protecting group is removed and the sterol derivative is prepared. The corresponding fluoro or bromo derivative of the sugar can also be reacted with the sterol. The method of converting a hexose to a 5-hydroxymethyl-D-aldohexose-based compound is accomplished by employing the following steps.

1. Enzymic Oxidation of D-aldohexose-based Compound with D-aldohexose:oxygen 6-oxidoreductase The reaction is conducted in a clean vessel under agitation. A mixer with a tip speed of about 100–400 feet/min is preferred. Sterile conditions prevent enzyme deactivation by microbial contamination.

An aqueous solution having a concentration of from about 1% to about 50%, preferably from about 10% to about 20% of D-aldohexose-based compound is prepared. The pH of the solution is adjusted to enhance reaction kinetics. A solution pH of from about 6 to about 8 is desired when using galactose oxidase as the enzyme. Galactose oxidase enzymic conversion requires a temperature of from about 1° C. to about 50° C. The reaction can be run at temperatures up to the inactivation temperature of the enzyme. However, at higher temperatures microbial growth can be an issue. A temperature of from about 3° C. to about 25° C. provides good enzyme stability, good oxygen saturation values at standard pressure, and reasonable reaction kinetics for galactose oxidase. Typical reaction times are in the range of from about 1 to about 24 hours.

From about 1,000 to about 1,000,000 unit activity of enzyme per mole of D-aldohexose or D-aldohexose based compound is typically added to the solution. Preferably from about 100,000 to 300,000 unit activity is used.

The level of available oxygen in solution also affects the oxidation step; a solution saturated with oxygen is preferred. Air and/or oxygen may be continuously bubbled through the solution to maintain oxygen saturation. Continuously pumping 2 to 3 volumes of air per volume of solution per minute using sparge rings having a high contact area works well. Suitable anti-foam agents include dimethyl silicone, other organosilicone compounds, and FG-10 silicone (Dow Chemical). The level of anti-foaming agent is from 10 to 100 ppm.

It is also advantageous to reduce or eliminate the amount of free peroxide in the reaction vessel. Adding from about 10,000 to about 2,000,000 unit activity of catalase per mole of D-aldohexose-based compound can be used. Other procedures for the removal of peroxide can be employed. Copper cations in the oxidation solution have been found to enhance enzyme stability. From about 0.1 mM to about 2 mM of $CuSO_4$ is used. Serum albumen is also a good enzyme stabilizer.

Finally, the catalase and D-aldohexose:oxygen 6-oxidoreductase are removed from the product solution. This can be done using conventional methods. The preferred separation technique is ultrafiltration through a membrane with from about 1,000 to about 30,000 molecular weight cut-off (MWCO).

2. Condensation of Oxidation Product With Formaldehyde to the 5-C-hydroxymethyl derivatives of D-galactose-based Compound From about 4 to about 40 molar equivalents of formaldehyde (most preferably from about 4 to about 8 molar equivalents) and from about 1 to about 13 molar equivalents of sodium hydroxide (most preferably from about 1 to about 3 molar equivalents) are added to the filtrate solution from step 1 (substrate). A resulting concentration of from about 10% to about 30% substrate is preferred. A pH between about 12 and about 13 is preferred. The reaction solution is maintained at a temperature of from about 15° C. to about 40° C. until completion of the reaction. Cooling may be required until the exothermic reaction has ceased (typically about 1 hour). The solution is agitated until the condensation reaction has achieved the desired degree of completion (about 1 to about 24 hours, typically 16 hours).

In order to control temperature and pH during the condensation reaction (thereby preventing aldehyde destruction), it is preferred to prereact the formaldehyde and sodium hydroxide in a separate operation. Aqueous formaldehyde and sodium hydroxide solutions are combined and agitated at from about 15° C. to about 35° C. until the exothermic reaction ceases (typically about 30 min.). The solution is then warmed to a temperature of from about 15° C. to about 40° C. and quickly added to the filtrate solution of step 1 while maintaining a temperature of from about 15° C. to about 40° C. The solution is agitated until the condensation reaction has achieved the desired degree of completion.

Other bases (e.g., $Ca(OH)_2$, KOH and mixtures of them) can be used in place of all or part of the sodium hydroxide.

Another method of conducting the condensation reaction with formaldehyde is through the reaction of the sugar aldehyde which is produced via the galactose oxidase oxidation reaction and formaldehyde on a strongly basic resin. The oxidation product and the formaldehyde are contacted with a resin which has a pH of at least 11.5 at a temperature of from about 20° C. to about 50° C. for from 0.5 to 24 hours. A ratio of formaldehyde to sugar aldehyde of 4:1 to 8:1 is used. Preferably the ratio is about 4:1 to about 5:1.

Sufficient salts and buffers are present in the oxidation reaction mixture to form and to maintain the highly basic conditions necessary to conduct the condensation reaction. As the reaction progresses, additional salts are generated from the formic acid formed and these are adsorbed by the resins. Use of methanol-free formaldehyde and cupric oxide as a catalyst facilitates the reaction.

The product of this reaction can be purified using fractional distillation to remove the excess formaldehyde and/or adsorption techniques in a manner similar to the other condensation reaction.

3. Purification

Unwanted ions (e.g., $Na^+, OH^-, H^+$) and residual formaldehyde should be removed from the resulting reaction solution. Purification can be accomplished by conventional means, such as by utilizing adsorption resins, dialysis, precipitation, or a combination of several techniques. Fractional distillation can also be use to effectively remove the formaldehyde.

4. Dewatering

The resulting solution from the above-mentioned purification step will generally contain from about 1% to 50% 5-C-hydroxy-methylated product. The purified aqueous product solution may be used directly, or it can be concentrated to higher levels (e.g., from about 90% to about 95% sugar).

It is desirable to concentrate the solution at low temperatures to prevent thermal breakdown of the 5-C-hydroxymethylated compound. Reverse osmosis employing a membrane with about a 100 MWCO and a 99% NaCl rejection at from about 10° C. to about 38° C. is preferred. Examples of these membranes include HR-98 or HR-99 polysulfone/polyamide thin film composite membranes, manufactured by Niro Corporation.

5. Crystallization

The most straightforward method of crystallizing 5-C-hydroxymethyl-aldohexose-based compounds is by saturating an aqueous solution at an elevated temperature and cooling it to precipitate out the product crystals. However, this technique can be hindered by impurities and by-products in the solutions. The following technique is the most effective for precipitating the product and reducing the level of impurities and by-products.

A 90–95% solution of the product compound is prepared. Water is removed using ethanol (1:1) additions/evaporations (usually 1 or 2 such procedures are sufficient).

The solid residue resulting from the final ethanol evaporation is dissolved in methanol under reflux; a ratio of 1:1 to about 3:1 of methanol to solid is used. This is followed by the cooling of the solution to from about −10° C. to about 20° C., for from about 1 to about 12 hours. The crystals are then filtered out and washed with cool methanol (about 0° C.).

Residual methanol may be removed by drying and/or by recrystallization from water. The crystals can be washed with acetone to further remove impurities.

The crystallization solvents can be removed by vacuum, fluidized bed drying and other techniques known in the art.

A detailed description of the synthesis of these compounds is found in the application of Mazur et al., EPO 341,063 (1989).

6. Acylation

First the 5-C-hydroxymethyl hexose is converted to an acylated 5-C-hydroxymethyl hexose to protect the sugar during subsequent reactions and to control the reaction products when the sugar is reacted with the sterol.

The 5-C-hydroxymethyl hexose is converted to the acylated derivative by a two-step esterification reaction. Any carboxylic acid anhydride can be used to make the esters.

Preferably the anhydrides of acids having from 2 to 6 carbon atoms are used. Most preferably, acetic anhydride is used to protect the hydroxyl groups.

The 5-C-hydroxymethyl hexose is reacted with an acid anhydride in the presence of a base. Pyridine, used as the solvent works well in this reaction. The reaction is usually carried out at ambient temperatures.

In this initial reaction, 4 of the hydroxyls are esterified in a monosaccharide and up to 6 or 7 hydroxyls of a disaccharide are acylated. The anhydro derivative of the sugar forms during this reaction.

The partially acylated sugar is then reacted with additional carboxylic acid anhydride and a catalytic amount of concentrated or anhydrous sulfuric acid. This opens the anhydro bridge and adds 2 more acyl groups. The 5-C-hydroxymethyl hexose is now fully acylated. The acylated derivatives are usually crystalline and are formed in good yield.

The acylation can be done in one step using an excess of acid anhydride and anhydrous or very concentrated acids, preferably sulfuric acid, as a catalyst. However, this process is not preferred.

By way of example, the following reaction conditions work best:
Temperature: Ambient.
Solvent: Pyridine.
Time: 1 to 24 hours.
Acid Anhydride:Carbohydrate Substrate Ratio: 1 to 2 equivalents for each hydroxyl group.

The partially acetylated sugar derivative or the 5-C-hydroxymethyl hexose can be esterified using acid catalyst under these conditions:
Temperature: 0° to 20° C.
Solvent: Acetic Anhydride.
Time: 1 to 24 hours
Catalyst: Concentrated sulfuric acid, phosphoric acid, or trifluoromethanesulfonic acid.

7. Condensation with Sterol

The hexaacylated hexose is coupled with the sterol by one of three pathways:

1. Reaction with sterol using trimethylsilyl trifluoromethanesulfonate.
2. Conversion to 1-bromo- derivative and then reacted with the sterol.
3. Conversion to 1-fluoro derivative and reacted with sterol.

In option 1, the sterol is mixed with the hexaacyl 5-C-hydroxymethyl hexose and trimethylsilyl trifluoromethanesulfonate in an inert solvent. Preferably chlorinated hydrocarbons are used as the solvent. A ratio of from 1:1 to 2:1 hexose to sterol is used. This reaction provides the pentaacyl 5-C-hydroxymethyl hexose sterol in yields of up to about 20%.

In option 2, an unstable 1-bromo pentaacyl 5-C-hydroxymethyl hexose is formed by reacting hydrogen bromide in acetic acid with the acylated sugar derivative. The bromo derivative is usually unstable and must be reacted immediately with the sterol and a catalyst. The reaction is run in smaller batches using chlorinated hydrocarbons as the solvent. It results in a 30% or less yield. Mercury cyanide works well as a catalyst in this reaction.

In option 3, a stable 1-fluoro-pentaacyl 5-C-hydroxymethyl hexose is formed by reacting the acylated hexose with pyridine and hydrogen fluoride. A possible side reaction involves cleavage of the acetyl group from the hexose 2-position. This hydroxyl group is easily reacylated by reacting the 1-fluoro compound with an acyl anhydride as described above.

The 1-fluoro derivatives prepared by this process are crystalline and stable. They can be crystallized from ethanol or other alkyl alcohols and stored. These materials make good sources of 5-C-hydroxymethyl hexose for derivatization of a number of materials. They are very reactive in coupling reactions with sterols.

The reaction of these stable 1-fluoro pentaacyl 5-C-hydroxymethyl hexoses with the sterol proceeds best when the sterol has been converted to the trimethylsilyl (TMS) derivative. The reaction with the TMS-sterol is run using chlorinated hydrocarbon solvents and boron trifluoride etherates as catalysts. The resultant product is a pentaacyl-5-C-hydroxymethyl hexose derivative of the sterol.

The pentaacyl derivatives of hydroxymethyl saponins are crystalline and easily purified by conventional techniques. The acyl groups are now hydrolyzed to make steryl 5-C-hydroxymethyl hexoside.

To hydrolyze the pentaacyl compounds, they are suspended in methanol or other lower alkyl alcohol and an alkali metal alcoholate (e.g., sodium methoxide) is added. This mixture is stirred for about 4–24 hours at ambient or reflux temperature.

The product is filtered and washed with alcohol. The product is a solid. The alcohol reactant and wash contain additional 5-C-hydroxymethyl hexose sterol derivatives which can be recovered by passing the alcohol through an amberlyst R120 acid (from Aldrich) form resin column until the alcohol (methanol) is neutral. The saponin is recovered from the alcohol eluent.

The sterol derivative can be dried under vacuum to remove any traces of solvent.

It has been found that the above reaction conditions provide good yields of hydroxymethyl saponins.

Method of Treatment

A safe and effective amount of the hydroxymethyl saponin is fed to animal or humans. Usually a dose of 5 to 600 mg/kg of body weight is used. Preferably this dose would be 5 mg/kg to 200 mg/kg and would be administered 1 to 4 times a day.

Solid dosage forms include tablets, capsules, granules, bulk powders, cookies or wafers and candy products. Tablets may contain suitable binders, lubricants, diluents, disintegrating agents, coloring agents, flavoring agents, flow-inducing agents and melting agents. Liquid oral dosage forms include aqueous solutions, emulsions, suspensions, solutions and/or suspensions reconstituted from non-effervescent granules and effervescent preparations reconstituted from effervescent granules. Such liquid oral dosage forms may contain, for example, suitable solvents, preservatives, emulsifying agents, suspending agents, diluents, sweeteners, melting agents, and coloring and flavoring agents. A preferred liquid dosage form is a juice-containing beverage or other beverage.

Specific examples of pharmaceutically acceptable carriers and excipients that may be used to formulate oral dosage forms of the present invention are described in U.S. Pat. No. 3,903,297, Robert, issued Sep. 2, 1975. Techniques and compositions for making dosage forms useful in the methods of this invention are described in the following references; *Modern Pharmaceutics*, Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2nd Edition (1976).

The 5-C-hydroxymethyl hexose sterols can also be used in combination with bile acid binders or cholesterol synthesis inhibitors, e.g. psyllium, cellulose, or cholestyramine.

The preparation of the 5-C-hydroxymethyl hexose sterols is described in the following examples. The examples are illustrative of the invention and are not intended to be limiting of it.

EXAMPLE I

Preparation of methyl 5-C-hydroxymethyl-α-L-arabino-hexopyranoside from methyl β-D-galactoside.

1. Oxidation of Methyl β-D-Galactopyranoside with Galactose Oxidase

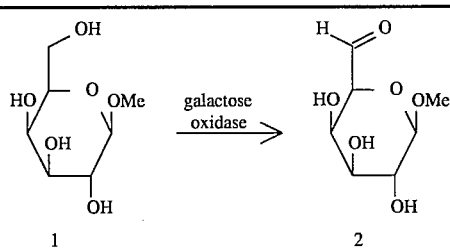

| Reagents | MW | Moles | Amount |
|---|---|---|---|
| methyl β-D-galactopyranoside Sigma Chemical Co., (No. M-6757) | 194.18 | 0.103 | 20.0 g |
| Phosphate Buffer, 100 mM | — | — | 412.0 ml |
| Catalase, 16900 units/mg Sigma Chemical Co., (No. C-40) | — | — | 7.5 mg |
| Galactose Oxidase | — | — | 9000 units |

The reaction is conducted in a one-liter vessel equipped with an aerator and a gentle stirrer. Sterile conditions are used to prevent enzyme deactivation by microbial contamination. The reaction is run at 4° C. to minimize deactivation of galactose oxidase.

Methyl β-D-galactopyranoside (1) is dissolved in the aerated phosphate buffer. The volume flow of air discharged by the aerator is regulated to produce an oxygen-saturated solution while preventing foaming of the solution. At 4° C., the galactose oxidase and catalase are added and this solution is aerated for 20 hours.

The enzymes are removed from the product solution by ultrafiltration using a 10,000 MWCO membrane (Diaflo 13242, manufactured by Amicon). The resulting filtrate contains the oxidation product, methyl β-D-galacto-hexodi-aldo-1,5-pyranoside (2).

2. Condensation of Oxidation Product With Formaldehyde to Methyl 5-C-Hydroxymethyl-α-L-arabino-hexopyranoside (3)

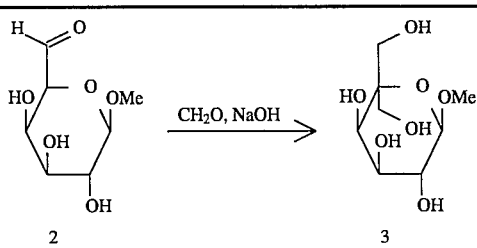

| Reagents | Amount |
|---|---|
| filtrate solution containing the oxidation product methyl β X⁻D-galacto-hexodialdo-1,5-pyranoside from step 1. | 400 ml |
| 37% formaldehyde solution (aqueous) | 400 ml |
| 50% sodium hydroxide solution (aqueous) | 144 ml |

The filtrate solution from step 1 and the formaldehyde solution are combined in a one-liter vessel. The sodium hydroxide solution is added to the filtrate/formaldehyde solution over a period of 1 hour while the solution temperature is maintained between 20° C. and 25° C. with an ice-water bath. After the exothermic reaction has ceased, the ice-water bath is removed and the reaction mixture is stirred at room temperature for 16 hours. The reaction mixture is heated to 55° C. and deionized using ion exchange columns: first Amberlite IR-120(H+), then Amberlite IRA-400(OH⁻), both packings manufactured by Rohm & Haas. Finally, the deionized solution of the product is eluted through an Amberlite IRA-400 (HSO₃⁻) ion exchange column to remove remaining formaldehyde. Slow room-temperature evaporation to dryness, followed by drying of the residue at room temperature under vacuum overnight produces 18.5 g (80%) of (3).

EXAMPLE II

Preparation of 1,6-anhydro-5-C-hydroxymethyl-β-L-altropyranose (4)

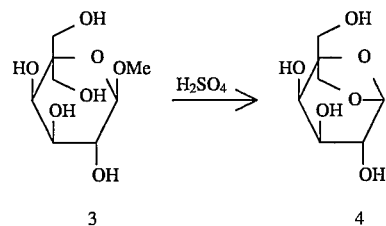

Methyl 5-C-hydroxymethyl-α-L-arabino-hexopyranose (3) (59.0 g, 0.263 moles) is dissolved in 0.70M sulfuric acid (260 ml), and stirred at 100° C. for 90 minutes. The solution is cooled to room temperature and neutralized using an ion exchange resin (Amberlite IRA-400 (OH⁻). The resin is filtered off, and the filtrate is refluxed for 15 minutes with activated carbon (4.0 g). Carbon is removed with a glass fiber filter, and the filtrate is evaporated to dryness with ethanol. The white waxy residue is refluxed for 15 minutes with methanol (50 ml). The solution is stored overnight at 0° C. The product is filtered to yield 20.0g (39.6%) of 1,6-anhydro-5-C-hydroxymethyl-β-L-altropyranose (4).

M.P.=166.5° C.–168.5° C. $[\alpha]_D^{23}$=+145.1 (C 7.2 in water)

EXAMPLE III

Preparation of 5-C-acetoxymethyl-1,2,3,4,6-penta-O-acetyl-L-arabino-hexopyranose (6)

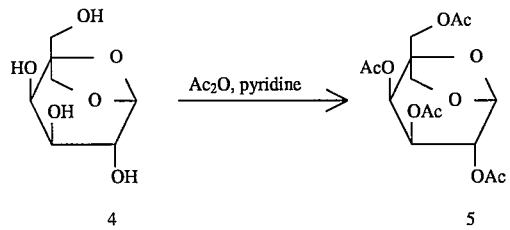

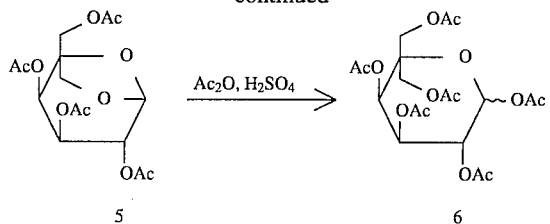

A solution of crude 1,6-anhydro-5-C-hydroxymethyl-β-L-altropyranose (4) (10.0 g, 52 mmol) in a mixture of acetic anhydride (100 ml) and pyridine (100 ml) is stirred at room temperature for 3 h. The reaction mixture is poured into ice water (300 ml), the product is extracted with methylene chloride (300 ml). The organic phase is washed with 1M HCl (3×400 ml), sodium bicarbonate (300 ml) and water (300 ml).

Evaporation of solvent produces crude 19.0 g of 5-C-acetoxymethyl-1,6-anhydro-2,3,4-tri-O-acetyl-β-L-altropyranose (5) which, without further purification, is dissolved in acetic anhydride (300 ml) and the solution is cooled to 0°–5° C. While maintaining this temperature, sulfuric acid (30.0 g) is slowly added. When the addition is complete, the ice bath is removed and the solution is stirred at ambient temperature for 2 h. At that time, TLC (Analtech GF plates, toluene:acetone 2:1) shows a single major product with a small amount of more polar impurities. An excess of acetic anhydride is destroyed by slow addition of water (45 ml) with cooling at temperatures below 30° C. The resulting solution is partitioned between methylene chloride (300 ml) and aqueous sodium bicarbonate (300 ml), the organic phase is washed repeatedly with sodium bicarbonate (3×300 ml) and water (300 ml). Evaporation of the solvent gives 17.0 g (70% yield) of (6).

$[\alpha]_D^{26.2} = +39.5°$ (C 8.3 in CHCl$_3$)

Anal. calc. for C$_{19}$H$_{26}$O$_{13}$: C, 49.35; H, 5.67. Found: C, 49.16; H, 5.60.

EXAMPLE IV

Synthesis of 5-C-acetoxymethyl-1-fluoro-2,3,4,6,-tetra-O-acetyl-L-arabino-hexopyranose (7)

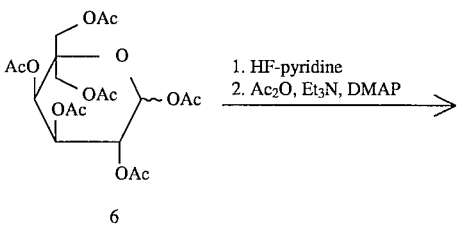

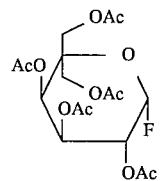

1,2,3,4,6,6'-Hexa-O-acetyl-5-C-hydroxymethyl-α/β-L-arabino-hexopyranose (74 g) is dissolved in cold (0° C.) HF-pyridine complex (200 g). A cooling bath is removed and stirring is continued until thin layer chromatographic analysis shows complete disappearance of the starting material (~3–4 h). The reaction mixture is diluted with methylene chloride (1.5 l) and the solution is washed with a saturated aqueous NaHCO$_3$ solution (2×300 ml) and brine (300 ml). The solution is dried over Na$_2$SO$_4$, filtered and solvents are concentrated to about 500 ml. Triethylamine (22 ml) and acetic anhydride (15 ml) are then added followed by 4-dimethylaminopyridine (50 mg) and the mixture is stirred at ambient temperature for about 1 h. The mixture is then diluted with methylene chloride (1.0 l), washed with NaHCO$_3$ aq. sat. solution (2×300 ml) and brine (300 ml), dried over Na$_2$SO$_4$ and filtered. The solvents are removed in vacuo and the crude product is crystallized (ethanol) to give 5-C-acetoxymethyl-1-fluoro-2,3,4,6,-tetracetyl-L-arabino-hexopyranoside (46.5 g).

EXAMPLE V

Diosgenin-5-C-acetoxymethyl-2,3,4,6,-tetra-O-acetyl-β-D-arabino-hexopyranoside (9)

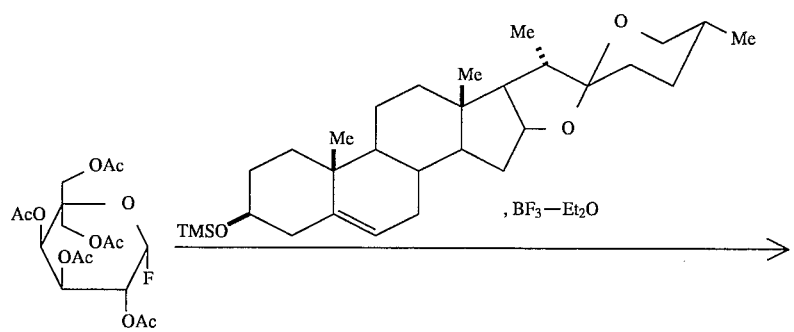

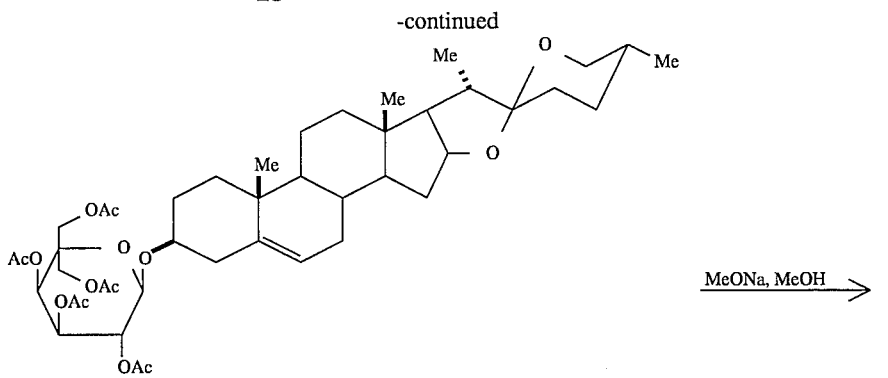

9

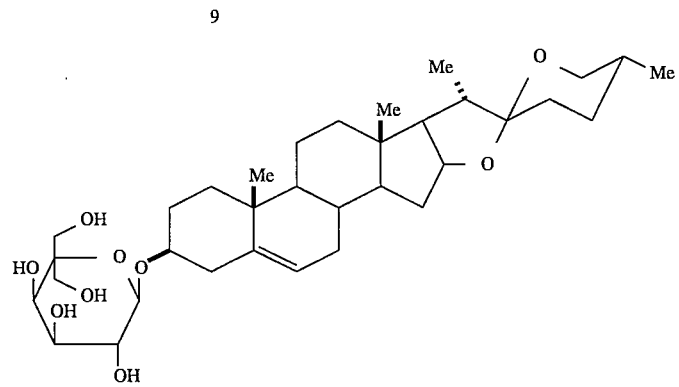

11

To a cold (0° C.) solution of 5-C-acetoxy-methyl 2,3,4,6-tetracetoxy-1-fluoro-L-arabino-hexopyranoside (12.7 g) and trimethylsilyldiosgenin (15 g) in dried 1,2-dichloroethane (300 ml) is added $BF_3 \cdot Et_2O$ complex (19.5 ml). The cooling bath is removed and the mixture is stirred for 1 h when TLC analysis shows complete disappearance of the fluoride. The reaction mixture is diluted with methylene chloride (300 ml), transferred to a separatory funnel and washed with $NaHCO_3$ aq. sat. solution (2×100 ml) and brine (100 ml). The solution is dried over $Na_2SO_4$, filtered and solvents are concentrated to about 100 ml. Triethylamine (4 ml) and acetic anhydride (2.5 ml) are then added, followed by 4-dimethylaminopyridine (10 mg) and the mixture is stirred at ambient temperature for about 1 h. The mixture is then diluted with methylene chloride (200 ml), washed with $NaHCO_3$ aq. sat. solution (2×100 ml) and brine (100 ml), dried over $Na_2SO_4$ and filtered. The solvents are then removed in vacuo and the crude product is purified by silica gel chromatography to give diosgenin 5-C-acetoxymethyl-2,3,4,6,-tetra-O-acetyl-β-D-arabino-hexopyranoside (11.8 g) as a white solid.

Hydrolysis to diosgenin-5-C-hydroxymethyl-β-D-arabino-hexopyranoside

This material is suspended in methanol (400 ml) and sodium methoxide (2 mL of 25% solution in methanol) is added. After stirring for 20 h at room temperature the mixture is filtered and thoroughly washed with methanol. The combined methanol washings are neutralized with Amberlite® IR-120 and solvent is evaporated. The solids are combined with the filtrant and dried in vacuo to give 8.22 g of diosgenin 5-C-hydroxymethyl-β-D-arabino-hexopyranoside.

EXAMPLE VI

Synthesis of diosgenin 5-C-hydroxymethyl-L-arabino-hexopyranoside

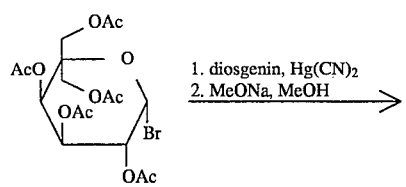

10

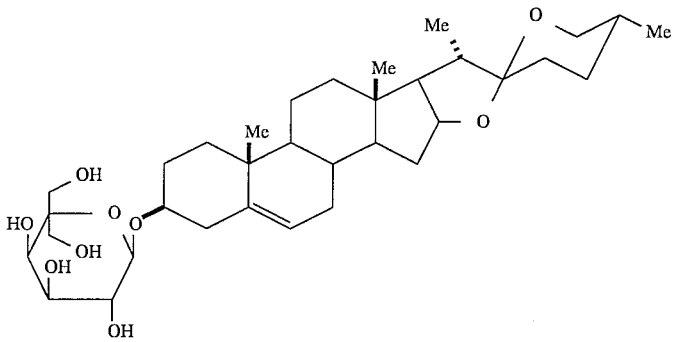

11

2,3,4,6-tetraacetyl-5-C-acetoxymethyl-1-bromo-L-arabinohexopyranoside prepared from per-O-acetyl-5-C-hydroxymethyl-L-arabinohexopyranose (18 g) according to the standard method, was mixed with diosgenin (12.3 g), mercuric cyanide (14.5 g) in dry 1,2-dichloroethane (250 ml) and stirred at 50° C. for 20 h. The reaction mixture was washed successively with water (1000 ml), 10% aqueous sodium iodide (2×200 ml), aqueous saturated solution of sodium bicarbonate (200 ml), and water (200 ml). The organic layer was next dried and evaporated. The crude residue was purified and hydrolyzed as described in Example V.

Evaluation as Hypocholesterolemic Agents

Four materials were compared using cellulose as a negative control and cholestyramine as a positive control. The saponins tested were diosgenin galactoside (DG), diosgenin-5-C-hydroxymethyl-L-arabino-hexopyranoside (DHG), cholesterol galactoside (CG) and 5-C-hydroxymethyl-arabino-hexopyranoside cholesterol (CHG).

Diet

The basal diet consisted of 0.2% (w/w) cholesterol (Byron Chemical Co., Long Island City, N.Y.) mixed with a 10% fat mix and ground chow (NIH-07) prepared by Research Diets, Inc. Cholestyramine resin (Sigma Chemical Co.), and Avicel PH-101 microcrystalline cellulose (FMC Corp.) were used. The final concentration of each of the test materials in the diets was 0.75% by weight.

Animals and Study Design

Male Golden Syrian hamsters, about 60 days of age (90–100 g), were obtained from Charles River Breeding Laboratories, Wilmington, Mass. The animals were pair-housed in plastic cages with raised bottom racks to limit coprophagy. On arrival the animals were fed a ground commercial chow (Purina Rodent Laboratory Chow #5001) and were acclimated to a reverse 12-hour light cycle (lights on 12:30 p.m.–12:30 a.m.). The animals were randomly assigned to six study groups of eight animals each, and were placed on test diets. One animal in the DG group was subsequently lost to study. Food and water consumption and body weights were recorded at least twice each week of the study. Randomization designated two successive start dates (seven or eight days of adaptation to the facility) and necropsy dates. A 7-day fecal collection was initiated after two days on the test diets. After 14 days on diet, the hamsters were individually anesthetized in random order in a carbon dioxide chamber. Blood was collected from the vena cava for blood lipid assays. These blood samples were refrigerated for not more than one hour before isolation of plasma. Plasma was isolated by refrigerated centrifugation.

Plasma Lipid Determinations

Cholesterol in plasma and HDL (precipitation method), and plasma triglyceride (corrected for free glycerol), were quantitated by enzymatic assays, using an automated clinical chemistry analyzer (Hitachi 705). Non-HDL cholesterol was calculated by difference.

Fecal Neutral Sterol Determination

Pooled 7-day fecal collections from each cage were homogenized in cold water by a Polytron, frozen, lyophilized, and powdered. Following 2:1 chloroform:methanol (Soxhlet) extraction, the lipids were recovered in the chloroform phase, dried to constant weight, then redissolved in chloroform. Aliquots of the extracts were spiked with 5-alpha cholestane (internal standard) and dried under nitrogen. Sterols were converted to trimethylsilyl ether (TMS) derivatives (Sylon BTZ, Supelco, Bellefonte, Pa.), and quantitated by GC/FID. The identification of cholesterol, coprostanol, and diosgenin in fecal extracts was confirmed by mass spectrometry. Coprostanone was a consistently minor cholesterol metabolite, and therefore was not quantitated. Total neutral sterol excretion therefore refers to the sum of fecal cholesterol and coprostanol.

Statistical Analyses

Statistical analyses were performed using SAS software. The data were analyzed as a randomized complete block, using necropsy day as a blocking factor. Fisher's least significant difference test (LSD) was employed for multiple comparisons when significant treatment effects ($\alpha=0.05$) were observed. Saponin structure-activity relationships were explored by two-way analysis of variance (diosgenin saponin vs. cholesterol saponin, and hydroxymethyl saponin vs. saponin). Results in the tables are expressed as mean±standard deviation.

Results

On all treatments, the hamsters appeared healthy and gained weight. There were no differences in food or water consumption, weight gain, or feed efficiency across groups. The average dose was 600 mg/kg/day.

Plasma cholesterol was significantly lower in all four groups treated with saponins relative to both controls (Table 1). While cholestyramine treatment did significantly lower plasma cholesterol levels by 12% vs. cellulose, the effect of saponins was greater, ranging from a 31.6% lowering (for CG) to 57.0% (for DHG). DHG was more effective than all other treatments at lowering plasma- and non-HDL cholesterol; CHG was more effective than CG. CG was the least effective saponin.

The saponins significantly increased the fecal excretion of cholesterol-derived neutral sterols, whereas cholestyramine had no effect on sterol excretion relative to cellulose (Table 2). DHG caused significantly higher cholesterol excretion compared to all other treatment groups. Total neutral sterol excretion was directionally higher with DHG vs. DG, although the difference did not achieve statistical significance.

The stability imparted to the glycosidic linkage by the presence of the 5-hydroxymethyl group on the sugar was studied by measuring fecal free diosgenin. The amount of free diosgenin was determined in the saponin preparations and in the fecal neutral lipid extracts from all treatment groups. Free diosgenin was not detected in the saponin preparations which were incorporated into the diets. Saponin intake was estimated from food consumption. Apparent in vivo hydrolysis was then calculated by dividing the molar excretion of fecal free diosgenin by the molar intake of saponin. Except for the four fecal extracts from the DG group and one extract from the derivatized saponin group, diosgenin concentrations in the extracts were below the standard curve. By full scan mass spectral analysis, positive purity determination for the fecal diosgenin peaks were only possible for the DG group's fecal extracts. Assuming that the low concentrations of diosgenin reported in the three saponins other than DG do represent diosgenin and are accurate, and using the average value for diosgenin excretion observed in the CG and CHG groups as baseline, the apparent in vivo hydrolysis averaged 12.5% for DG, compared to 0.5% for DHG.

By two-way analysis of variance, the 5-C-hydroxymethyl saponins were significantly more effective than the non-derivatized saponins for lowering plasma cholesterol ($p<0.0001$) and non-HDL cholesterol ($p<0.002$). Diosgenin-containing saponins were also more effective than cholesterol-containing saponins. The superior stability of the glycosidic linkage imparted by the 5-C-hydroxymethyl group could reasonably be presumed to contribute to the superior performance of diosgenin saponin vs. cholesterol saponin, in that hydrolysis of CG would liberate cholesterol.

In conclusion, 5-C-hydroxymethyl saponins exhibited superior efficacy vs. their non-derivatized saponin counterparts. Based on the fecal free diosgenin measurements, the 5-C-hydroxymethyl group substantially improves the stability of the glycosidic linkage. This increased stability results in the finding of superior efficacy for the derivatized saponins.

In Tables I & II the following abbreviations are used:
CSTYR=cholestyramine
CELL=cellulose
DG=diosgenin galactoside
DHG=diosgenin 5-C-hydroxymethyl-L-arabino-hexopyranoside
CG=cholesterol galactoside
CHG=cholesterol 5-C-hydroxymethyl-L-arabino-hexopyranoside

TABLE 1

| Variables | Plasma Lipids | | | | | |
|---|---|---|---|---|---|---|
| | DG | DHG | CG | CHG | CSTYR | CELL |
| Plasma-C (mg/DG) | 125 ± 13 | 102 ± 11 | 162 ± 15 | 134 ± 17 | 208 ± 16 | 237 ± 23 |
| Non HDL-C (mg/dL) | 44 ± 5 | 26 ± 4 | 60 ± 9 | 45 ± 9 | 114 ± 18 | 136 ± 22 |
| HDL-C (mg/dL) | 81 ± 2 | 76 ± 7 | 102 ± 18 | 89 ± 10 | 94 ± 7 | 102 ± 16 |
| Trig (mg/dL) | 123 ± 12 | 105 ± 34 | 141 ± 44 | 112 ± 36 | 162 ± 65 | 142 ± 44 |

TABLE 2

| Variables | Fecal Neutral Lipids | | Saponins | | | |
|---|---|---|---|---|---|---|
| | Cell | CSTYR | DG* | CG | DHG | CHG |
| Fecal Dry Wt. (g/ham/day) | 1.57 ± 0.29 | 1.41 ± 0.34 | 1.53 ± 0.07 | 1.62 ± 0.28 | 1.58 ± 0.32 | 1.54 ± 0.09 |
| Fecal Lipids (% dry weight) | 8.2 ± 0.8 | 8.2 ± 0.3 | 12.1 ± 0.2 | 12.5 ± 0.3 | 11.3 ± 1.6 | 11.4 ± 1.6 |
| Coprostanol (mg/ham/day) | 2.0 ± 0.2 | 2.2 ± 0.7 | 4.8 ± 0.5 | 1.20 ± 0.4 | 2.9 ± 1.0 | 1.2 ± 0.2 |
| Cholesterol (mg/ham/day) | 1.0 ± 0.3 | 0.8 ± 0.3 | 9.2 ± 1.5 | 8.6 ± 1.0 | 13.2 ± 3.7 | 8.7 ± 0.8 |
| Total Neutral Sterol (mg/ham/day) | 3.1 ± 0.4 | 3.0 ± 1.0 | 14.0 ± 1.1 | 9.8 ± 1.0 | 16.2 ± 4.6 | 10.0 ± 0.7 |
| Free Diosgenin (mg/ham/day) | 0.15 ± 0.08** | 0.21 ± 0.06** | 5.88 ± 0.61 | 0.60 ± 0.08** | 0.74 ± 0.10** | 0.50 ± 0.60** |

*For one box in the DG group, per day measurements are based on 10 hamster-days, versus 14 for all other animal boxes.
**These values for diosgenin are estimates, as they fell below the standard curve.

What is claimed is:

1. A sterol 5-C-hydroxymethyl glycoside compound wherein the glycoside is selected from the group consisting of 5-C-hydroxymethyl glucose and 5-C-hydroxymethyl galactose and their acylated derivatives and the sterol is selected from the group consisting of diosgenin, tigogenin and cholesterol, wherein the glycoside is attached at the 3-position of the sterol via a glycosidic linkage.

2. A compound according to claim 1 wherein the sterol is diosgenin.

3. A compound according to claim 1 wherein the sterol is tigogenin.

4. A compound according to claim 1 wherein the sterol is cholesterol.

5. A method of lowering the blood plasma cholesterol level in an animal or human comprising feeding the animal or human a safe and effective amount, in unit diosage form, of a sterol 5-C-hydroxymethyl gltycoside wherein the glycoside is selected from the group consisting of 5-C-hydroxymethyl glucose and 5-C-hydroxymethyl galactose and their acylated derivatives and the sterol is selected from the group consisting of diosgenin, tigogenin and cholesterol, wherein the glycoside is attached at the 3-position of the sterol via a glycosidic linkage.

6. A method according to claim 5 wherein the sterol is tigogenin.

7. A method according to claim 5 wherein the sterol is diosgenin.

8. A method according to claim 5 wherein the sterol is cholesterol.

9. A method according to claim 5 or 7 wherein the unit dosage form is a solid.

10. A method according to claim 5 or 7 wherein the unit dosage form is a liquid.

11. A method according to claim 5 or 7 wherein the compound is administered at a level of 5 to 200 mg/kg body weight.

12. A method of treating atherosclerosis in an animal or human comprising feeding the animal or human a safe and effective amount, in unit dosage form, of a sterol 5-C-hydroxymethyl glycoside wherein the glycoside is selected from the group consisting of 5-C-hydroxymethyl glucose and 5-C-hydroxymethyl galactose and their acylated derivatives and the sterol is selected from the group consisting of diosgenin, tigogenin and cholesterol, wherein the glycoside is attached at the 3-position of the sterol via a glycosidic linkage.

13. A method according to claim 12 wherein the sterol is tigogenin.

14. A method according to claim 12 wherein the sterol is diosgenin.

15. A method according to claim 12 wherein the sterol is cholesterol.

16. An acylated compound of any one of claims 1, 2, 3 and 4 wherein all hydroxy moieties of the glycoside are acylated.

17. An acetylated compound of any one of claims 1, 2, 3 and 4 wherein all the hydroxy moieties of the glycoside are acetylated.

* * * * *